United States Patent
Wiffen (10) Patent No.: US 12,257,176 B2
(45) Date of Patent: Mar. 25, 2025

(54) ADJUSTABLE ORAL DEVICES FOR PREVENTING OR REDUCING SNORING OR OBSTRUCTIVE SLEEP APNEA (OSA)

(71) Applicant: Aria Healthcare Limited, Ellesmere Port (GB)

(72) Inventor: Richard Wiffen, Ellesmere Port (GB)

(73) Assignee: Aria Healthcare Limited, Ellesmere Port (GB)

( * ) Notice: Subject to any disclaimer, the term of this patent is extended or adjusted under 35 U.S.C. 154(b) by 0 days.

(21) Appl. No.: 17/352,452

(22) Filed: Jun. 21, 2021

(65) Prior Publication Data

US 2021/0307956 A1     Oct. 7, 2021

Related U.S. Application Data

(63) Continuation of application No. 15/741,699, filed as application No. PCT/GB2016/052059 on Jul. 8, 2016, now Pat. No. 11,051,973.

(30) Foreign Application Priority Data

| Jul. 8, 2015 | (GB) | 1511916 |
| Jan. 26, 2016 | (GB) | 1601449 |
| Feb. 10, 2016 | (GB) | 1602386 |

(51) Int. Cl.
    *A61F 5/56*     (2006.01)
    *A61C 7/08*     (2006.01)
    *A61F 5/58*     (2006.01)

(52) U.S. Cl.
    CPC .......... *A61F 5/566* (2013.01); *A61F 5/56* (2013.01); *A61F 5/58* (2013.01); *A61C 7/08* (2013.01)

(58) Field of Classification Search
CPC .... A61F 5/56; A61F 5/566; A61F 5/58; A61F 2005/563; A63B 71/085; A61C 7/08; A61C 5/90
USPC .............. 128/859, 860, 861, 862; 433/6
See application file for complete search history.

(56) References Cited

U.S. PATENT DOCUMENTS

| 5,868,138 A | 2/1999 | Halstrom |
| 6,109,265 A | 8/2000 | Frantz et al. |
| 7,810,502 B1 | 10/2010 | Nguyen et al. |

(Continued)

FOREIGN PATENT DOCUMENTS

| JP | 2012040136 A | * | 3/2012 | |
| WO | WO-2009062541 A1 | * | 5/2009 | ............. A61F 5/566 |

OTHER PUBLICATIONS

Translation of WO 2009/062541 A1 (Year: 2009).*

(Continued)

*Primary Examiner* — Alireza Nia
*Assistant Examiner* — Daniel A Miller
(74) *Attorney, Agent, or Firm* — Vedder Price P.C.

(57) ABSTRACT

A device (10) having a body (12) informed from as a one-piece single unit having a first tray portion (16) for receiving the upper dental arch of the oral cavity of the wearer and a second tray portion (14) for receiving the lower dental arch of the oral cavity of the wearer. Integrally formed therewith and connecting the two tray portion s are two connecting portions (18), (20) which are flexible and the two tray section are of a design or material or combination of design and material selected to achieve retention of the trays on the teeth of a user.

12 Claims, 10 Drawing Sheets

(56) References Cited

U.S. PATENT DOCUMENTS

| | | | | |
|---|---|---|---|---|
| 8,839,793 B2* | 9/2014 | Diaz | ................. | A61C 7/08 |
| | | | | 128/848 |
| 2011/0226261 A1* | 9/2011 | Hernandez | ............. | A61F 5/566 |
| | | | | 128/848 |
| 2014/0352701 A1* | 12/2014 | Ingemarsson-Matzen | ................. | |
| | | | | A61F 5/566 |
| | | | | 128/848 |

OTHER PUBLICATIONS

Translation of JP 2012040136 A (Year: 2012).*
Preliminary Report on Patentability issued in connection with PCT/GB2016/052059 on Jan. 18, 2018; 9 pgs.

* cited by examiner

ADJUSTABLE ORAL DEVICES FOR PREVENTING OR REDUCING SNORING OR OBSTRUCTIVE SLEEP APNEA (OSA)

CROSS-REFERENCE TO RELATED APPLICATION

This application is continuation of U.S. patent application Ser. No. 15/741,699, filed Jan. 3, 2018, which is a National Stage Entry of PCT/GB2016/052059 filed Jul. 8, 2016, the entire disclosure of which is incorporated herein by reference.

FIELD OF THE INVENTION

The present invention relates to oral devices for preventing or reducing snoring and/or Obstructive Sleep Apnea (OSA), kits of parts and a method of assembling mandibular advancement devices.

BACKGROUND OF THE INVENTION

Snoring and OSA are associated conditions with heavy snoring being a common indicator of the presence of OSA. Snoring is caused by air turbulence resulting from the vibration or disruption of the tissue and structure of the upper airway. Such disruption of the tissue and structure of the airway may extend to the point of causing multiple events of closure or obstruction of the upper airway characteristic of OSA Snoring is often a source of sleep disruption to the bed partner of the snorer resulting in impairment of sleep and relationship. In the long term snoring, even when not immediately associated with the presence of OSA, may cause inflammation, swelling and damage to the tissue of the upper airway that may in turn encourage the development of OSA. Reduction in snoring is of benefit to both the sufferer and the bed partner and where that snoring is a precursor or indicator of OSA there is an imperative to seek treatment.

There are various alternative treatments offered to manage the snoring condition with various evidence of success. Most pharmacy products seek to address the condition of mucosal tissue. There is limited evidence as to the effectiveness of such products. The only treatment to reduce snoring that currently has widespread acceptance of a high degree or likelihood of effectiveness is oral device therapy. Oral devices with a mechanism for mandibular advancement act on the muscles supporting the airway and physically sustain airway patency.

Solid state interface devices, such as touch pads and touch screens, are popular and in use on a wide variety consumer electronic products and motor vehicle systems. However, these solid state interface devices typically fail to provide a user with any form of tactile feedback as a result of their solid state nature. The human user of the interface device therefore is not able to experience haptic sensations that assist and inform the user during interaction with the interface device.

Additionally, oral devices have emerged as an alternative to continuous positive airway pressure (CPAP) for OSA. There is a strong evidence base demonstrating that oral devices improve OSA in the majority of patients, particularly those with mild to moderate OSA but also some sufferers with severe OSA. Oral devices are generally well tolerated, although short-term adverse effects during acclimatization are common. Long-term dental changes may occur, but these are for the most part subclinical and do not preclude continued use. Patients often prefer oral device use to gold-standard CPAP treatment. Although most head-to-head trials confirm CPAP as superior in reducing OSA parameters on polysomnography this greater efficacy does not necessarily translate into better health outcomes in clinical practice. Comparable effectiveness of oral devices and CPAP has been attributed to higher user compliance and acceptance of oral device use as compared with CPAP use.

Oral devices fall broadly into either of two categories. Firstly there are custom devices specific to the patient based on taking a physical impression of the patient's teeth or more recently from a digital scan image of the teeth. Such oral devices generally offer good levels of comfort and retention on the teeth. However they are expensive and that expense may prove inadvisable if the patient discovers that they are unable to tolerate overnight wearing of the device or they are one of the approximately 15% of patients for whom an oral device is not effective.

Thermo-formable devices, generally known as boil-and-bite, are a much less expensive alternative to custom devices and offer a sensible route to first purchase and for many people may become the only device they require.

Although there is a plethora of oral device designs most share a common design strategy of advancing the lower jaw or mandible. Custom devices and boil-and-bite devices often share this same design feature and mechanism of action. Studies comparing the effectiveness of custom devices with boil-and-bite devices have generally concluded that custom devices are more effective. However the detail of these studies frequently indicate that the higher degree of effectiveness of custom devices is not down to any superior mechanism of action but primarily down to greater retention on the teeth.

With oral devices, advancing the mandible is generally achieved by positioning the lower tray, sometimes called the lower portion, forward of the neutral position vis-a-vis forward of the upper tray or upper portion. This is usually achieved by some form of connection between the upper and lower tray which fixes the lower tray or portion in a forward position so that when the device is placed in the oral cavity the lower teeth sit forward of the natural bite position of the wearer.

Better designs of oral devices have a means of varying the extent of the advancement of the lower tray. This is important, firstly because the natural bite position varies from person to person and secondly because the degree of advancement necessary to treat the snoring or OSA varies from individual to individual and even varies in the same individual over time.

Designs with a variable advancement mechanism broadly fall into three categories; those where the mechanism is located at the side of the device, those where the mechanism is located at the front of the device, those where the mechanism is located towards the rear of the device.

An example of a device design where the mechanism is located at the side of the device is disclosed by patent U.S. Pat. No. 6,109,265 and marketed as the Myerson EMA. The advantage of such designs is that as well as achieving mandibular advancement they allow the jaw to move relatively freely in an upwards/downwards direction, sometimes referred to as movement in the sagittal plane. The disadvantages of such designs are firstly that the majority of them achieve mandibular advancement through the use of linkage rods or straps. These are of fixed length and varying the amount of mandibular advance is usually achieved by replacing rods or straps of one length with those of a different length. Unless well designed the rods or straps and particularly the connection points can protrude into the cheek wall causing discomfort and even inflammation. The second disadvantage of these designs is that because the rods or straps are located in parallel down each side of the device they restrict the ability of the jaw to move from side to side, sometimes referred to as movement in the transverse plane.

An example of a device design where the advancement mechanism is located at the front of the device is disclosed by patent U.S. Pat. No. 5,868,138, other devices include the TAP 3 device.

Such a design will achieve mandibular advancement and may allow for a mechanism that is less bulky than a mechanism located at the side of the device and the mechanism generally will not protrude into the cheek wall causing discomfort and inflammation. The first disadvantage of such a design is that it will not permit the jaw to move upwards or downwards, through the sagittal plane. The second disadvantage is that although such devices allow for side-to-side movement of the device in the transverse plane the pivot point of the device will be at the front whereas the mandible pivots at the back of the oral cavity so the device is not sympathetic to the movement of the jaw.

An example of a device design where the advancement mechanism is located at the close to the rear of the device is the Apnea RX device.

Such a design will achieve mandibular advancement and may allow for a mechanism that is less bulky and the mechanism generally will not protrude into the cheek wall causing discomfort and inflammation. The first disadvantage of such a design is that it will only permit at best limited and at worst no movement upwards or downwards of the jaw, through the sagittal plane. The second disadvantage of such a design is that it will only permit at best limited and at worst no movement side-to-side of the jaw, through the transverse plane.

A departure from designs that position the lower tray forward of the neutral position vis-a-vis the upper tray by some form of connection between the upper and lower tray is disclosed by U.S. application Ser. No. 14/308,636 (Ingemarsson-Matzen) In this design there is a fixed position resilient hinge located at the rear (mid-way point) of the device. Advancement of the jaw is achieved by either a mechanism located solely on the upper tray to reduce the distance between the front apex of the upper tray and the fixed position resilient hinge (decrease the length of the upper tray) or a mechanism located solely on the lower tray to increase the distance between the front apex of the lower tray and the fixed position resilient hinge (increase the length of the lower tray) A key component of this design is a resilient hinge of sufficient robustness to be capable of resisting the force exerted by the muscles of the jaw seeking to return the jaw to its natural bite position. The advantage of such a design is that it permits good upwards or downwards movement of the jaw, through the sagittal plane. The disadvantage of such a design is that a resilient hinge will only permit at best very limited and at worst no movement side-to-side of the jaw, through the transverse plane.

A variation on the Ingemarsson-Matzen design is U.S. Pat. No. 7,810,502 (Nguyen). This also features a fixed position hinge mechanism located at the rear of the upper tray. The hinge comprises a tubular member embedded in the upper tray and a wire running through the tubular member and attached to the lower tray. Advancement of the jaw/mandible is achieved by mechanism located on the lower tray and acting on the wire and intended to increase the distance between the front apex of the lower tray and the fixed position tubular member part of the hinge (increase the length of the lower tray). As with the Ingemarsson-Matzen design the advantage of the Nguyen design is that it permits good upwards or downwards movement of the jaw, through the sagittal plane. The disadvantage of the design is that the tubular member hinge and wire will only permit at best very limited and at worst no movement side-to-side of the jaw, through the transverse plane.

Any device that by its design limits natural movement of the jaw in any plane will result in one of two or a combination of two undesirable effects. Firstly the force exercised by the jaw seeking to move in a direction restricted by the design of the device will act to pull the device away from the teeth causing the device to fall loose. Alternatively the grip of the device on the teeth may be stronger than the force exercised by the jaw in which case the wearer will suffer an element of discomfort. This may be sufficient over time to cause temporomandibular disorders (sometimes called TMD or TMJD) in some cases.

It will be appreciated that such devices which are of the boil and bite type are more likely to be less close fitting and therefore simply fall out when such force is exercised by the jaw. Such devices which are custom fitted are more likely to be tighter fitting and therefore more likely to cause discomfort when such force is exercised and in the long term possibly temporomandibular disorders.

It has also been noted that devices that achieve advancement by a mechanism fixing the upper tray to the lower tray do not permit desirable movement of the mandible vis-a-vis the maxilla in an up and down or side to side direction. One alternative to devices that fix the upper tray to the lower tray are devices utilizing a resilient hinge. Such devices, however, are poor at allowing side to side movement.

In accordance with a first aspect of the present invention, there is provided an oral device comprising a first tray portion for receiving at least a portion of the upper dental arch of the oral cavity of a wearer and a second tray portion for receiving at least a portion of the lower dental arch of the oral cavity of the wearer, the tray portions together with or connected by flexible members or sections capable of assuming a folded configuration within the oral cavity wherein the first tray portion at least partially overlies the second tray portion, and wherein associated with each flexible member or section is an adjustment method capable of operating or acting on or across the flexible member for determining the apex of the fold when the device is in its folded configuration such that the location of the apex of the fold determines the relative position of the first tray portion with respect to the second tray portion in the folded configuration.

The present invention overcomes and/or addresses one or more of the limitations of all the aforementioned designs in enabling movement both in the sagittal and transverse planes whilst providing a simple mechanism for adjustment in the coronal plane. The present invention takes advantage of the fact that the jaw is itself a hinge and that a unitary device fitted to the upper and lower teeth will if the device is sufficiently flexible fold round to adapt to the oral cavity. The natural fold or apex of the curve will be at the point determined by the fact that the device is fixed to the upper and lower teeth. For a person with a neutral bite position the pivot point will be close to halfway along the overall length of the device.

Varying the location of the fold point by a mechanism proximate to and acting directly on or across each of the flexible members in the present invention will change the relative position of the tray portions to one another in use and therefore the relative positions of the mandible and maxilla. By incorporating an adjustable mechanism or assembly proximal to the flexible portion and acting on or across each of them of the device a plurality of alternative fold points may be provided.

An advantage of an adjustment mechanism that can change the fold point of the flexible members is that any change in the fold point has a twofold change in the advancement of the lower tray vis-a-vis the upper tray and consequently the advancement of the jaw/mandible. Thus each 1 mm change in the fold position will effect a 2 mm change in the advancement of the lower tray vis-a-vis the upper tray. This may, for example, be contrasted with the Ingemarsson-Matzen and Nguyen designs where a 1 mm increase of the distance between the front apex of the lower tray and the fixed position hinge results in only an overall 1 mm change in the advancement of the lower tray vis-a-vis the upper tray. As the space to locate any adjustment mechanism and the size of such mechanism is constrained by the small free areas between the device and the teeth, cheeks and tongue the current invention allows for a greater range of jaw/mandible advancement for size of mechanism compared with other designs.

The ability to advance the mandible is a requirement of an effective oral device for treating snoring and sleep apnoea. The flexible members or sections of the present invention not only permit movement in the sagittal plane but also permit lateral movement of the tray portions relative to one another greatly improving the comfort of a wearer when the device is used. The device may comprise two flexible members one on each side of the device integrally formed with the tray portions.

The device may comprise alternative discrete flexible members. The use of a discrete flexible member permits the flexible member to be readily made of an alternative material to that of the tray portion; a feature particularly useful when the tray portion is formed from a dental impression to create a custom device.

The discrete members and the tray portions may have mating means so that the flexible members may mate with the first and second tray portions.

The mating members may comprise any one or more of the following: hook and loop, adhesive means, and tongue and groove.

Suitably, the mating members may be complementarily shaped with respect to one another. More suitably the flexible members may have male mating means disposed thereon and the tray portions have female mating means disposed thereon. The device may have adjustment means comprising a support member mounted on a tray portion and an adjustable member moveably mounted on the support member such that the adjustment member is capable of adopting a plurality of configurations for determining a plurality of locations for the apex of the fold when the device is in a folded configuration.

The adjustment member may be capable of translational movement with respect to the support member. Suitably, the support member may comprise a lug.

The adjustment member may comprise a pin having a threaded shaft and a rounded head against which the flexible member may abut in the folded configuration. Suitably, the adjustment means may be mounted on the second tray portion.

The adjustment member may be mounted by means of adhesive, rivet and or over moulding or other known means of securing two materials together. Suitably, mounting is by means of overmoulding. The adjustment member may have one or more flaps which will sit below the surface of tray portion which is overmoulded over the adjustment member.

The adjustment means is capable of dictating the maximum forward or rearward displacement of the first tray vis-a-vis the second tray and vice versa when the device is folded and in situ on the teeth.

The flexible member or portion may comprise or may be overlaid, inlaid or reinforced by a more robust and less malleable or other alternative material than the material used for the trays. The material may comprise polyethylene terephthalate resins commonly known as PET or BOPET or a similar material having an element of resilient spring return force.

The device may further comprise reinforcement means at the fold to provide reinforcement. The reinforcement means may comprise a resiliently deformable member. The resiliently deformable member may be manufactured from a material comprising any one or more of polyethylene terephthalate resins commonly known as PET or BOPET or a similar material. The resilient member may provide spring return force at the fold point which may help retain the device in situ in use by biasing the first tray portion towards the maxilla as the resilient member will bias the device into its unfolded configuration.

In accordance with an aspect of the present invention there is provided an oral device comprising a first tray portion for receiving at least a portion of the upper dental arch of the oral cavity of a wearer and a second tray portion for receiving at least a portion of the lower dental arch of the oral cavity of the wearer, the tray portions together with or connected by flexible members or sections capable of assuming a folded configuration within the oral cavity wherein the first tray portion at least partially overlies the second tray portion, and wherein associated with each flexible member or section is an adjustment means capable of contacting said flexible member for determining the apex of the fold when the device is in its folded configuration wherein the location of the apex of the fold determines the relative position of the first tray portion with respect to the second tray portion in the folded configuration, and wherein at least a portion of at least one adjustment means is capable of contact with the flexible members or sections when in a folded configuration to determine the location of the apex of the fold.

In accordance with a further aspect of the present invention, there is provided a kit of parts for mandibular advancement comprising an oral device as described hereinabove and a plurality of discrete flexible members of varying lengths. The adjustment means is mounted partly on the flexible member or section and partly on the first tray portion or the second tray portion.

In accordance with a further aspect of the present invention, there is provided a method of assembling an oral device as described hereinabove comprising selecting a discrete flexible member of desired length and connecting the first and second tray portion with said flexible member.

In accordance with an aspect of the present invention there is provided an oral device comprising a first tray portion for receiving at least a portion of the upper dental arch of the oral cavity of a wearer and a second tray portion for receiving at least a portion of the lower dental arch of the oral cavity of the wearer, the tray portions together with or connected by flexible members or sections having a folded configuration wherein the first tray portion at least partially overlies the second tray portion, and wherein associated with each flexible member or section is an adjustment means which contact the flexible member or section to determine the apex of the fold when the device is in its folded configuration such that the location of the apex of the fold determines the relative position of the first tray portion with respect to the second tray portion.

DESCRIPTION OF THE DRAWINGS

The present invention will now be described, by way of example only, with reference to the accompanying drawings, in which.

Figure 1:
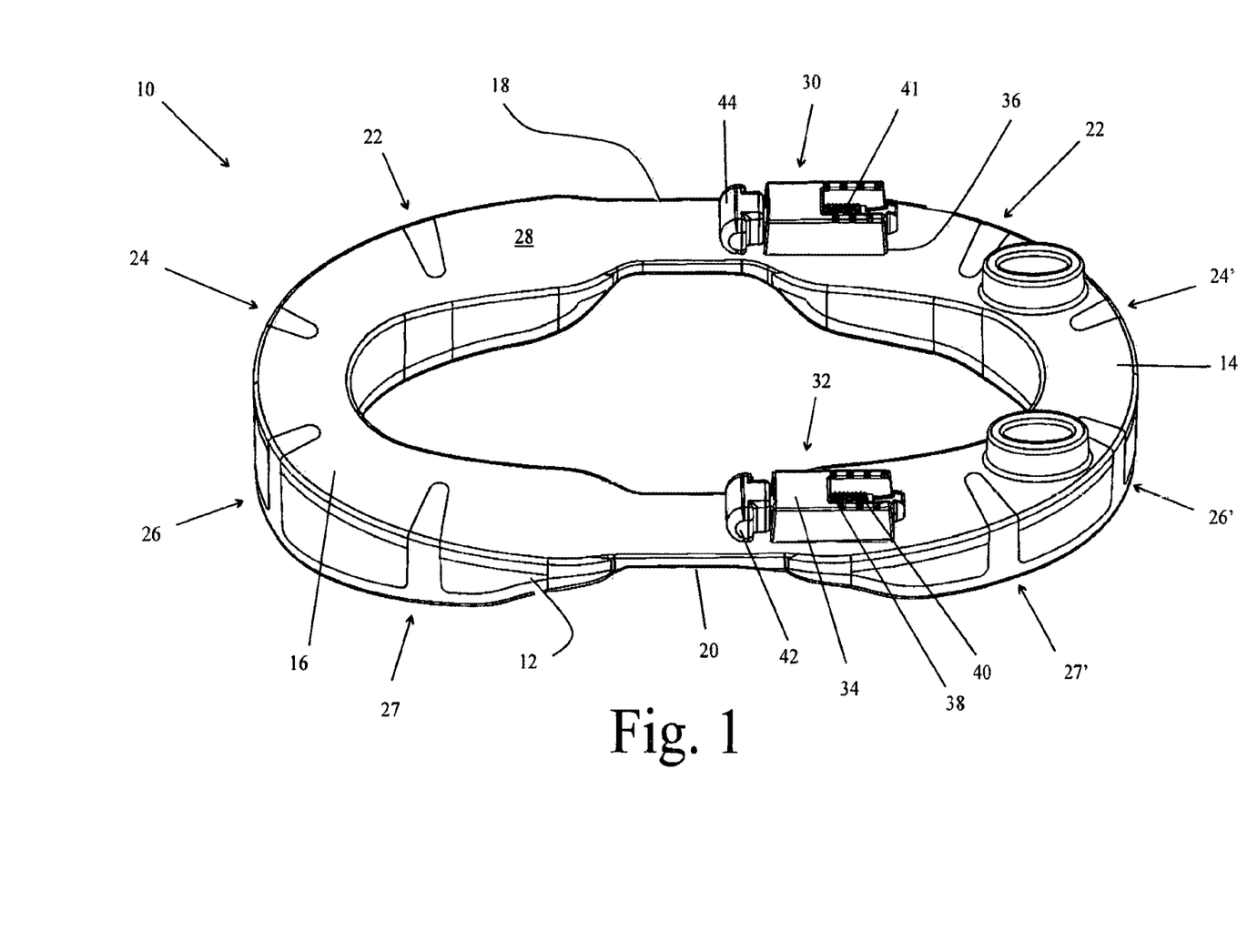
FIG. 1 shows a device in accordance with the present invention.

FIG. 1 shows a device 10 having a body 12 formed from as a one-piece single unit having a first tray portion 16 for receiving the upper dental arch of the oral cavity of the wearer and a second tray portion 14 for receiving the lower dental arch of the oral cavity of the wearer. Integrally formed therewith and connecting the two tray portions are two connecting portions 18, 20 which are flexible and the two tray sections are of a design or material or combination of design and material selected to achieve retention of the trays on the teeth.

The first and second tray portion have a number of spaced apart indents 22,24,26,27 and 22'24'26'27' respectively which overlie one another when the device is folded and in a neutral position. The indents permit the trays to flex and better conform to the shape of a wearer's upper and lower dental arch. Disposed on a first surface 28 of the device, said surface 28 being substantially planar, is a pair of adjustment assemblies 30, 32 each having a lug 34 extending perpendicularly from a planar base 36 mounted on or partially into the first surface 28 of the device. Each lug 34 has a threaded bore 38 which receives the free end 40 of a threaded shaft 41 of an adjustment screw 42. At the other end of the threaded shaft is the rounded head 44 of the adjustment screw 42 which has a series of longitudinal ridges to provide grip when adjusting the distance between the lug 34 and the rounded head 44. Adjusting the distance between the lug and rounded head in this way will dictate the point at which the connectors will fold and as such the relative off set between the first tray portion and the second tray portion in use.

Figure 2A:
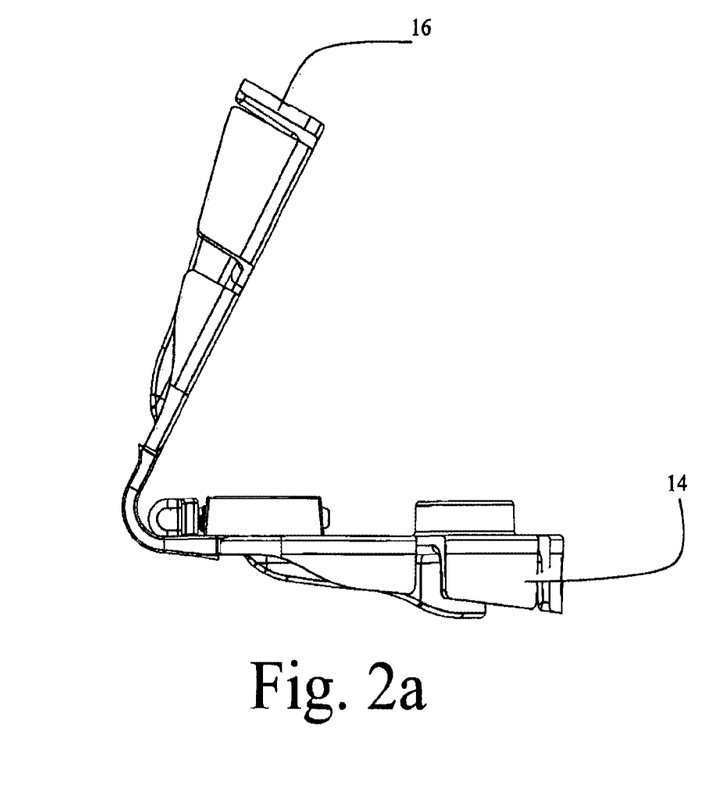
FIGS. 2a and b show the device of FIG. 1 folded.
Figure 2B:
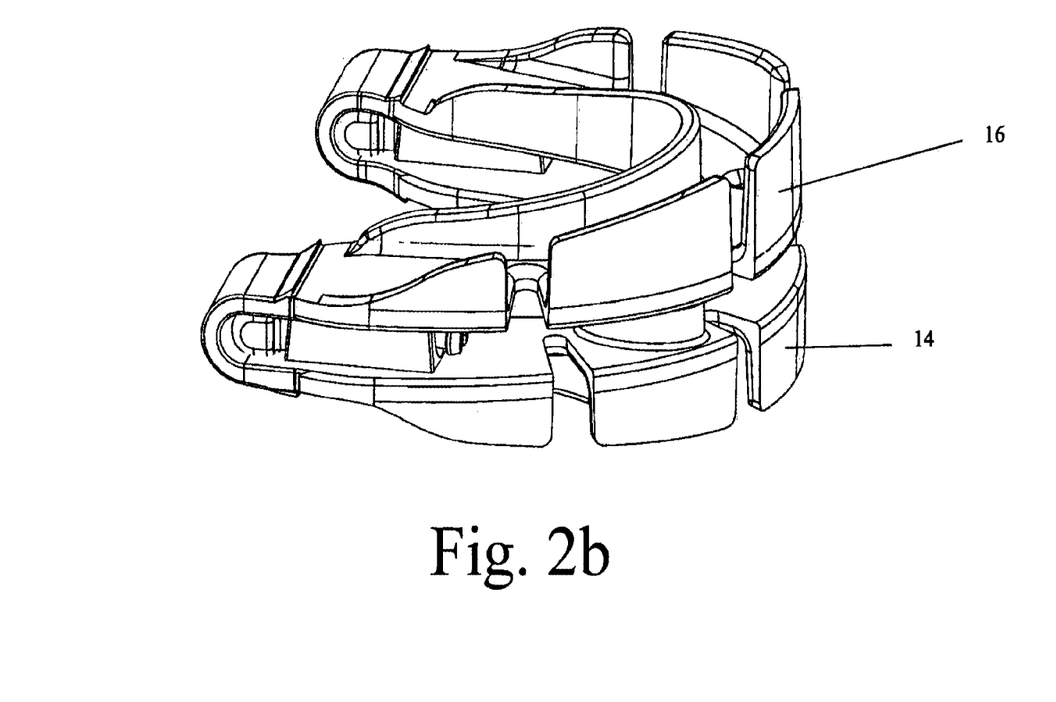

FIGS. 2a and b show the device folded.

Figure 3A:
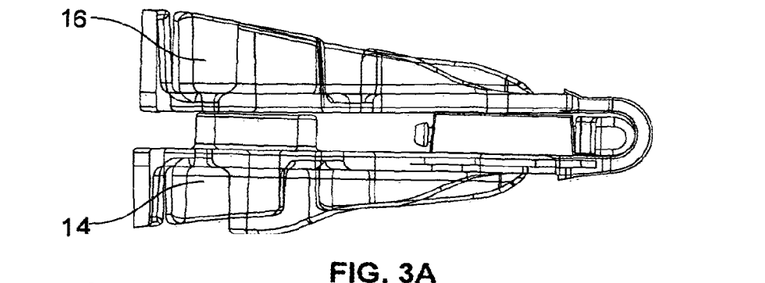
FIGS. 3a to c show the device of FIG. 1 folded and the advancement of the upper or lower tray relative to one another in accordance with displacement of the adjustment means.
Figure 3B:
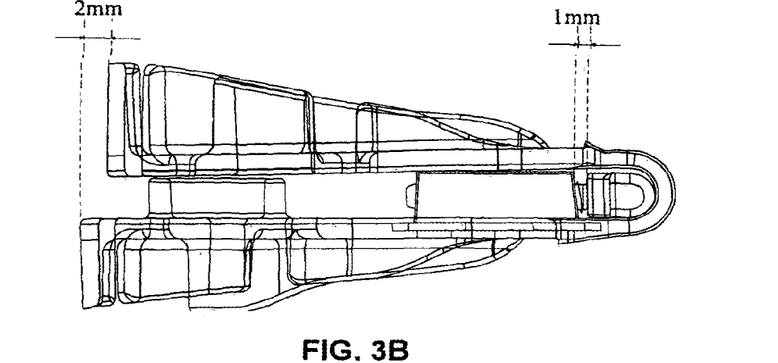
Figure 3C:
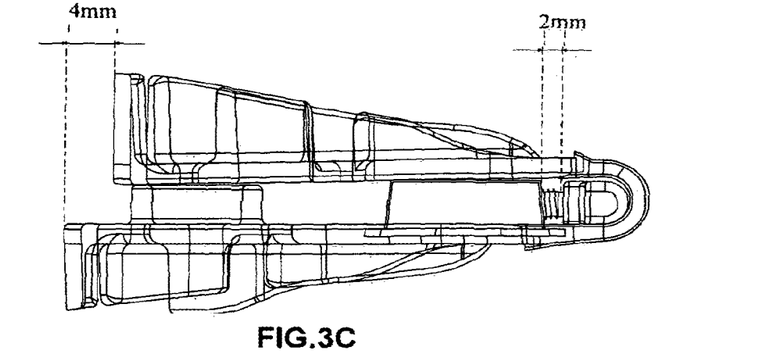

FIGS. 3a to c show that that displacement of the adjustment mechanism has a twofold change in the advancement of the lower tray vis-a-vis the upper tray and consequently the advancement of the jaw/mandible or vice versa. Thus each 1 mm change in the fold position will effect a 2 mm change in the advancement of the lower tray vis-a-vis the upper tray or vice versa. As stated above, this may, for example, be contrasted with the Ingemarsson-Matzen and Nguyen designs where a 1 mm increase of the distance between the front apex of the lower tray and the fixed position hinge results in only an overall 1 mm change in the advancement of the lower tray vis-a-vis the upper tray. As the space to locate any adjustment mechanism and the size of such mechanism is constrained by the small free areas between the device and the teeth, cheeks and tongue of the present invention may allow for a greater range of jaw/mandible advancement for size of mechanism compared with other designs, as set out in FIGS. 3a to c.

FIGS. 4a to d show the device folded and the adjustment means dictating the location of the fold and thus the relative positions of the first and second tray portions with respect to one another. Owing to the flexibility of the connecting portions, the adjustment means in fact dictate the maximum displacement possible between the first and second tray portions.

Figure 4A:
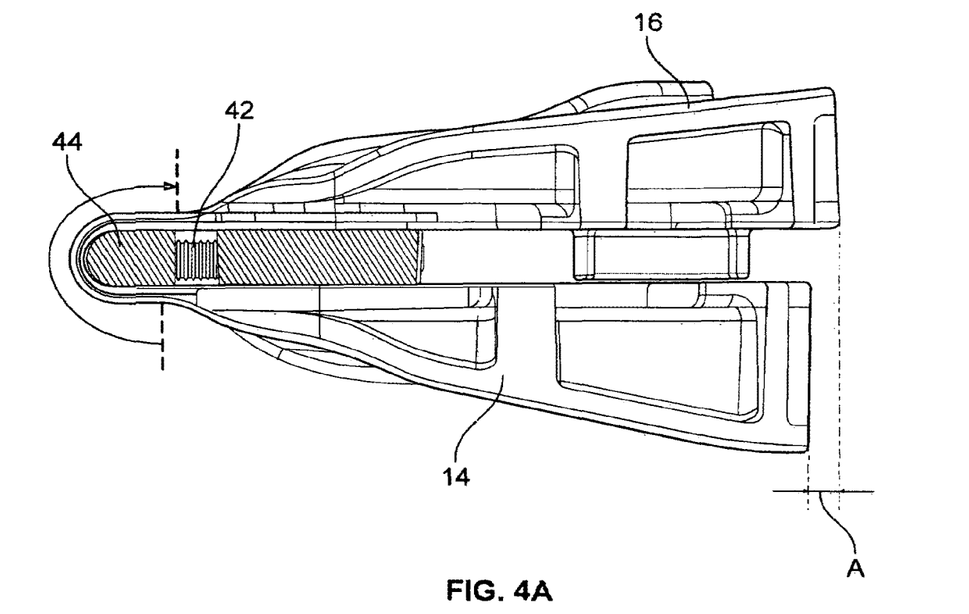
FIGS. 4a to d show a device in accordance with the present invention in different configurations.

FIG. 4a shows the configuration where the first tray portion partially overlies the second tray portion. The first tray portion is off-set by distance 'A' from the second tray portion. Distance 'A' is dictated by the co-operation between the adjustment screws 42 and the connectors 18,20. The position of the adjustment means and in particular the head 44 of the adjustment screw 42 will dictate where the fold of the connectors 18, 20 will be when in use. The adjustment means is capable of dictating the maximum forward or rearward displacement of the first tray vis-a-vis the second tray and vice versa when the device is folded and in situ on the teeth. Depending upon the desired effect the maximum displacement of the relative positions of the mandible and maxilla may be dictated by the adjustment means.

The arrow shows the direction of displacement of the tray portions with respect to one another from a neutral position. This displacement can either be rearward or forward from the neutral position.

The rounded head 44 of the adjustment screw 42 rests against the first surface 28 of the connectors 18, 20.

Figure 4B:
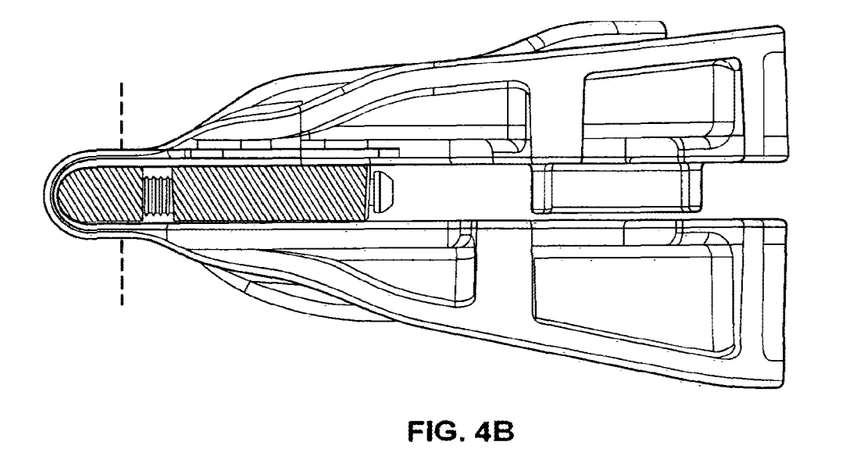

FIG. 4a shows the lower tray marginally displaced rearwards, distance A, from the upper tray portion FIG. 4b shows a neutral position where there is no displacement of the relative positions of the upper or lower tray portions.

Figure 4C:
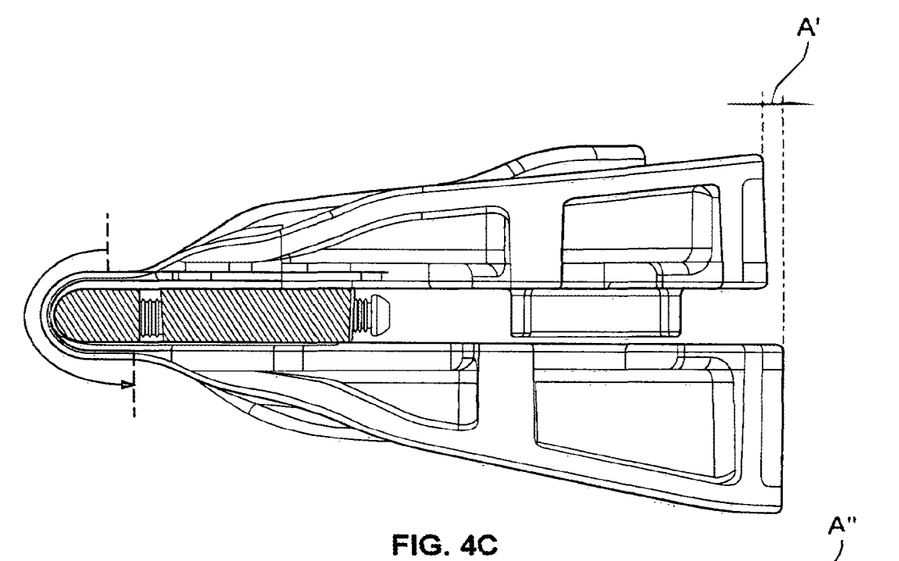

FIG. 4c shows the lower tray portion marginally displaced forwards, distance A', from the upper tray portion.

Figure 4D:
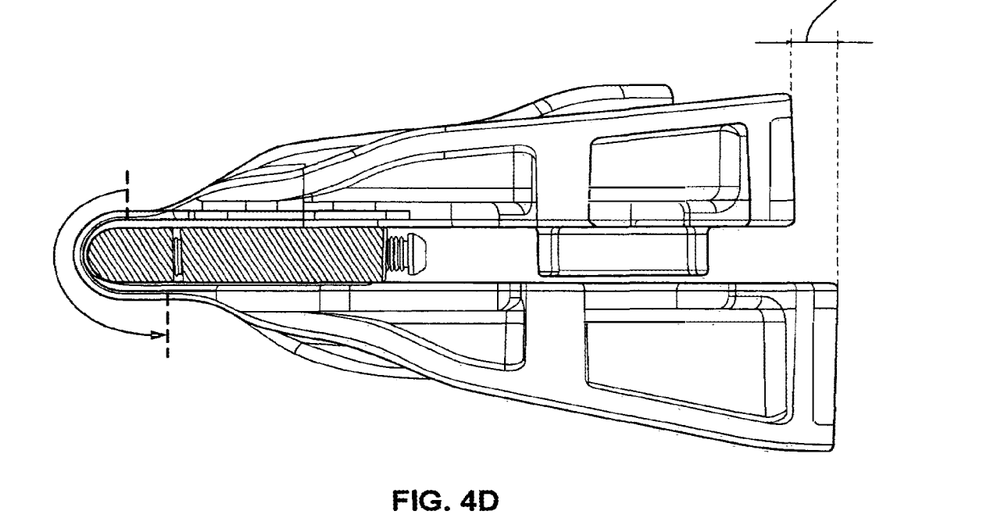

FIG. 4d shows the lower tray portion further displaced forwards, distance A", from the upper tray portion than that shown in FIG. 3c.

Representative distances illustrated are A=4.5 mm (rearward); A'=3 mm (forward); and A"=6 mm (forward).

As previously stated, the present invention takes advantage of the fact that the jaw is itself a hinge and that a unitary device fitted to the upper and lower teeth will if the device is sufficiently flexible fold round to adapt to the oral cavity. In the absence of an adjustment mechanism the natural fold or apex of the curve will be at the point determined by the fact that the device is fixed to the upper and lower teeth.

For a person with a neutral bite position the pivot point will be close to halfway along the overall length of the device.

By including an adjustable mechanism or assembly proximal to the flexible portion of the device and capable of operating or acting on or across each flexible member a plurality of fold points may be provided. Varying the location of the fold point will change the distance from the apex of the fold to the end point of the upper tray and the end point of the lower tray-increasing one of these distances and decreasing the other. Varying the fold point will also change the relative position of the tray portions to one another in use and therefore the relative positions of the mandible and maxilla. The further back the adjustment screw is advanced away from the lug 34 and the first tray portion 14 (which rests on the lower dental arch in use) the further forward the mandible will be displaced relative to the maxilla when the device is worn. FIGS. 3a to c shows such displacement. This particular embodiment shows the mechanism having an adjustment screw but there are numerous alternative incremental or successive mechanisms known to the skilled person that could be adapted to achieve the same objective of varying the fold point and which are encompassed in the scope of the present invention.

Figure 5:
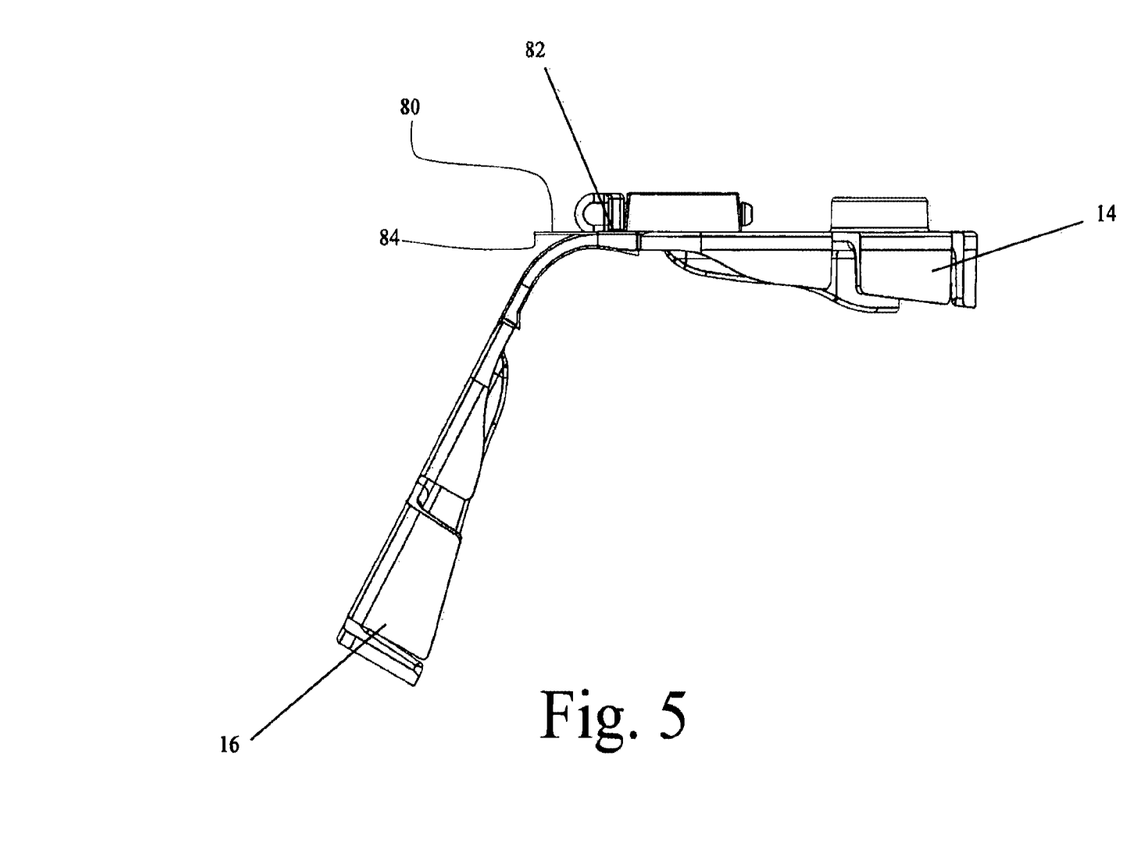
FIG. 5 shows a device in accordance with the present invention having alternative adjustment means.

FIG. 5 shows one side of another embodiment having two reinforcement members 80 (only one shown) each associated with an adjustment assembly. The reinforcement members may have a resiliently deformable planar body connected at one end 82 to the adjustment assembly. The free end 84 of the reinforcement member 80 lies over the flexible member or section and when the device is folded, the reinforcement member provides additional resistance to folding thereby urging the upper tray into the maxilla to better assist in retaining the device in situ.

Alternatively the reinforcement member may be connected on both the top and bottom parts of the assembly. Alternatively the material may be to add strength rather than resilience to the adjustment assembly.

The present invention provides an oral device of sufficient flexibility that it is capable of readily folding around a curve at any point over a distance of about 20 mm close to the mid-point of the device and sufficient strength that it will not deform or break down as it folds around a mechanism or assembly. Happily many materials are known in the art, examples include EVA, LOPE, TPU, SEBS, SEPS which are already available and have such qualities and doubtless new materials will be added to this group over time.

In another embodiment (FIG. 6), there is a device 100 whose principal difference with the device 10 shown in FIGS. 1, 2 and 3 is that the integrally formed flexible connectors 18, 20 are replaced with discrete flexible connectors 102, 104. The flexible connectors 102, 104 have a substantially rectangular body with an upper surface 106 which lies flush with the first surface 128 of the device 100 in use.

Figure 6:
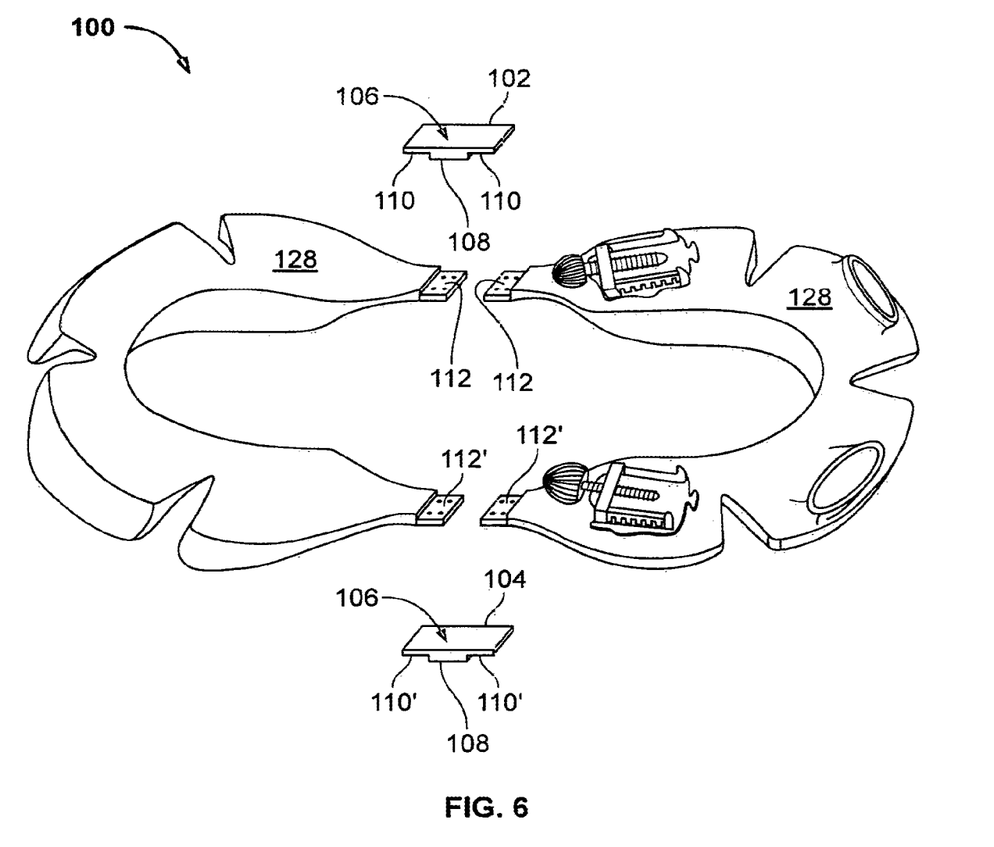
FIG. 6 shows a device in accordance with the present invention.

The connectors 106, 108 have a substantially planar upper surface 106 and lower surface 108. At either end of the connector 106, 108 are the first members 110, 110' of a mating pair. The second members 112, 112' of the mating pair is located on the first and second tray portions. The first and second members comprise correspondingly shaped recess edges of the connectors and tray portions such that when mated the upper surfaces of the connectors and tray portions are flush with one another and in substantially the same plane, and the lower surfaces of the surfaces of the connectors and tray portions are flush with one another and in substantially the same plane.

The tray portions are shown in FIG. 6 to have disposed on the recessed edge a plurality of blind bores which are correspondingly shaped to receive a plurality of protrusions disposed on the recessed edge of the connectors. Other means envisaged by the skilled person by which the connectors and the tray portions may mate are encompassed in the present invention, such as hook and loop mating, adhesive means, tongue and groove, etc.

The length of the connectors can be varied in other embodiments such that the device is effective on any sized mandible and maxilla, and a custom fit for a user may be provided.

The material of the connectors can be varied from that of the trays to optimize the comfort and strength of the respective parts as appropriate to their function.

Figure 7:
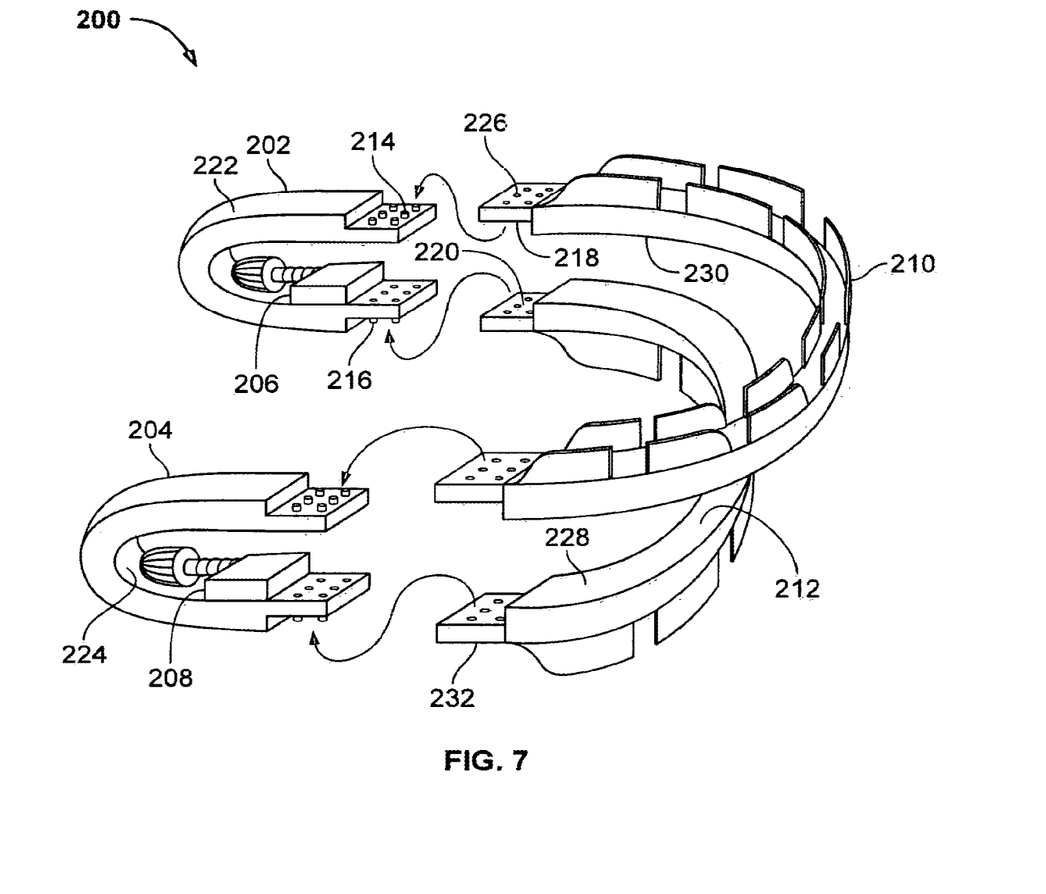
FIG. 7 shows a device in accordance with the present invention.

In another embodiment (FIG. 7), there is a device 200 whose difference with the device 10 shown in FIGS. 1 to 4 is that the connecting portions 18, 20 are separate discrete flexible connectors 202, 204 upon which are mounted the adjustment assemblies 206, 208. The discrete connectors are mateable with the upper and lower tray portions 210,212 by means of male and female mating members. The male mating members 214, 216 are disposed at either end of the discrete of the discrete connector 202, 204 and are complementarily shaped to the female mating members 218, 220 disposed on the upper and lower tray portions respectively. The upper 222 and lower surface 224 of the flexible connectors 202, 204 are flush with upper 226, 228 and lower 230, 232 surfaces of the tray portions when the device is assembled.

In another embodiment (FIG. 8), there is a device 300 whose difference with the device 10 shown in FIGS. 1 and 2 is the adjustment mechanism. The pair of adjustment assemblies 30, 32 are replaced by a linear track 302 with asymmetrical teeth 304, and a stop 306 that engages the teeth 304. The teeth are uniform but asymmetrical, with each tooth having a moderate 'gentle' slope on one edge and a much steeper slope on the other edge.

Figure 8:
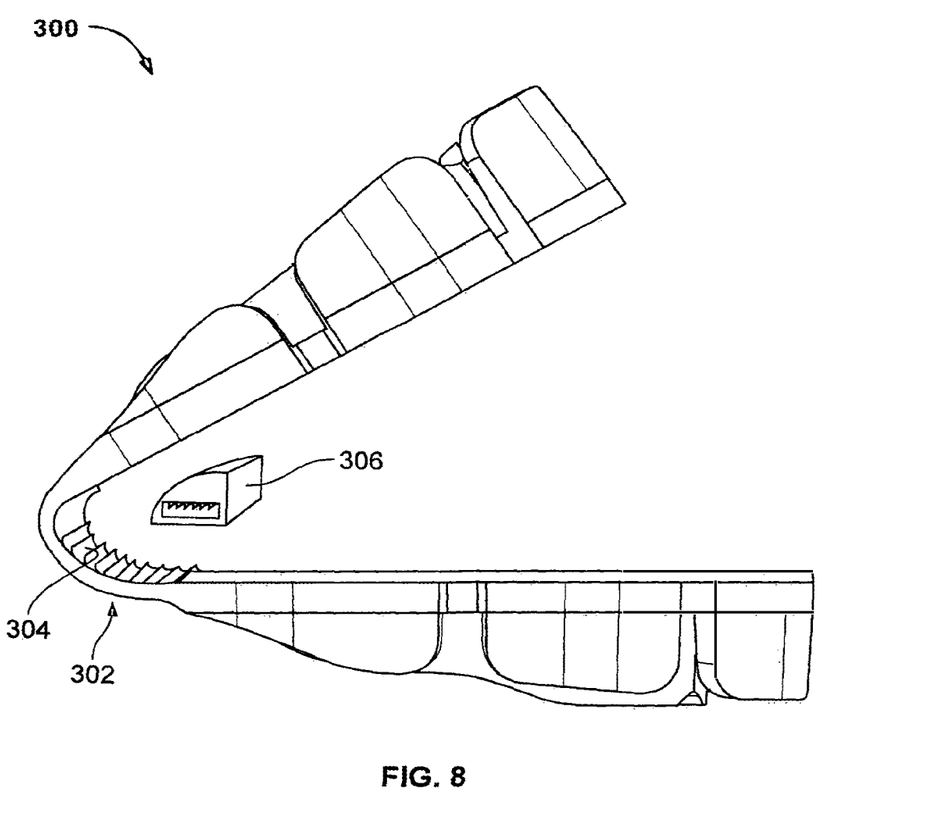
FIG. 8 shows a device in accordance with the present invention.

When the teeth are moving in the unrestricted (i.e., forward) direction, the stop easily slides up and over the gently sloped edges of the teeth, with a spring forcing it (often with an audible 'click') into the depression between the teeth as it passes the tip of each tooth. When the teeth move in the opposite (backward) direction, however, the pawls will catch against the steeply sloped edge of the first tooth it encounters, thereby locking it against the tooth and preventing any further movement in that direction.

The above features and advantages of the present invention will become apparent from the following detailed description taken with the following drawings.

What is claimed is:

1. An oral device comprising a first tray portion (16) configured for receiving at least a portion of an upper dental arch of an oral cavity of a wearer and a second tray portion (14) configured for receiving at least a portion of a lower dental arch of the oral cavity of the wearer, the first and second tray portions (14, 16) connected by two foldable flexible members or sections (18, 20) which are integrally formed with the first and second tray portions, the foldable flexible members or sections and the first and second tray portions further comprising mating means adapted to engage with each other;
  wherein the first and second tray portions (14, 16) together with the foldable flexible members or sections (18, 20) are capable of assuming a folded configuration within the oral cavity; and
  associated with each of the foldable flexible members or sections (18, 20) is an adjustment means (30, 32) which determine an apex of the fold of each flexible member or section (18, 20) when the oral device is in the folded configuration and thereby determine a relative position of the first tray portion (16) and the second tray portion (14) to the apex of each fold and of each tray portion to the other;
  wherein a location of a fold point of the foldable flexible members or sections by the adjustment means will determine the relative position of the first and second tray portions;

wherein the first tray portion (16) at least partially overlies the second tray portion (14), wherein the adjustment means (30, 32) are capable of contacting said foldable flexible members or sections (18, 20) to determine the apex of the fold when the oral device is in the folded configuration such that the location of the apex of the fold determines the relative position of the first tray portion (16) with respect to the second tray portion (14) in the folded configuration, and wherein said adjustment means (30, 32) are capable of creating the apex of the fold at variance with the location that would otherwise be determined by the natural bite position of the wearer.

2. The oral device as claimed in claim 1, wherein the foldable flexible members or sections are discrete flexible members or sections.

3. The oral device as claimed in claim 2, wherein each of the foldable flexible members or sections mate with the first and second tray portions; and or, wherein the mating means are complementarily shaped with respect to one another; and or, wherein the mating means comprise any one or more of the following: hook and loop, adhesive means, and tongue and groove; and or, wherein each of the foldable flexible members or sections have male mating means disposed thereon and the first and second tray portions have female mating means disposed thereon.

4. The oral device as claimed in claim 1, further comprising a biasing means for biasing the oral device into an unfolded configuration; and or, wherein the biasing means comprises one or more resilient members disposed proximal to each of the foldable flexible members or sections; and or, wherein the one or more resilient members overlie the each foldable flexible member or section; and or, wherein the one or more resilient members are integrally formed with each of the foldable flexible members or sections.

5. The oral device as claimed in claim 4, wherein the biasing means comprises any one or more of the following: polyethylene terephthalate resins commonly known as PET or BOPET or a similar material; and or, wherein the biasing means is connected to the adjustment means.

6. The oral device as claimed in claim 1, wherein the adjustment means is mounted on the second tray portion; and or, wherein the adjustment means is mounted on each of the foldable flexible members or sections such that the adjustment member is capable of adopting a plurality of configurations for determining a plurality of locations for the apex of the fold when the oral device is in the folded configuration.

7. The oral device as claimed in claim 1, wherein each of the foldable flexible members or sections comprises a material less malleable than the first or second tray portion; or wherein each of the foldable flexible members or sections comprises a first and second material, where the second material is less malleable than the first or second tray portions and or the first material, and the second material is overlaid on the first material of each of the flexible members or sections.

8. A kit of parts for mandibular advancement comprising the oral device as claimed in claim 1, and a plurality of the flexible members or sections of varying lengths.

9. A method of assembling the oral device as claimed in claim 1, further comprising selecting a flexible member or section of a desired length and connecting the first and second tray portions with said flexible member or section.

10. An oral device comprising a first tray portion (16) configured for receiving at least a portion of an upper dental arch of an oral cavity of a wearer and a second tray portion (14) configured for receiving at least a portion of a lower dental arch of the oral cavity of the wearer, the first and second tray portions (14, 16) connected by two foldable flexible members or sections (18, 20) which are integrally formed with the first and second tray portions, the foldable flexible members or sections and the first and second tray portions further comprising mating means adapted to engage with each other;

wherein the first and second tray portions (14, 16) together with the foldable flexible members or sections (18, 20) are capable of assuming a folded configuration within the oral cavity; and associated with each of the foldable flexible members or sections (18, 20) is an adjustment means (30, 32) which determine an apex of the fold of each flexible member or section (18, 20) when the oral device is in the folded configuration and thereby determine a relative position of the first tray portion (16) and the second tray portion (14) to the apex of each fold and of each tray portion to the other;

wherein a location of a fold point of the foldable flexible members or sections by the adjustment means will determine the relative position of the first and second tray portions;

wherein the adjustment means comprises a support member mounted on the first tray portion or the second tray portion and an adjustment member moveably mounted on the support member such that the adjustment member is capable of adopting a plurality of configurations for determining a plurality of locations for the apex of the fold when the oral device is in the folded configuration; and wherein the adjustment member comprises a pin having a threaded shaft (41) and a rounded head (44) against which the flexible members or sections abut in the folded configuration.

11. The oral device as claimed in claim 10, wherein the adjustment member is capable of translational movement with respect to the support member; and or, wherein the support member comprises a lug (34).

12. An oral device comprising a first tray portion (16) configured for receiving at least a portion of an upper dental arch of an oral cavity of a wearer and a second tray portion (14) configured for receiving at least a portion of a lower dental arch of the oral cavity of the wearer, the first and second tray portions (14, 16) connected by two foldable flexible members or sections (18, 20) which are integrally formed with the first and second tray portions, the foldable flexible members or sections and the first and second tray portions further comprising mating means adapted to engage with each other;

wherein the first and second tray portions (14, 16) together with the foldable flexible members or sections (18, 20) are capable of assuming a folded configuration within the oral cavity; and associated with each of the foldable flexible members or sections (18, 20) is an adjustment means (30, 32) which determine an apex of the fold of each flexible member or section (18, 20) when the oral device is in the folded configuration and thereby determine a relative position of the first tray portion (16) and the second tray portion (14) to the apex of each fold and of each tray portion to the other;

wherein a location of a fold point of the foldable flexible members or sections by the adjustment means will determine the relative position of the first and second tray portions;

wherein the adjustment means are each mounted partly one of the foldable flexible members or sections and partly on the first tray portion or the second tray portion such that the adjustment member is capable of adopting a plurality of configurations for determining a plurality of locations for the apex of the fold when the oral device is in the folded configuration.

\* \* \* \* \*